(12) United States Patent
Yeh et al.

(10) Patent No.: US 8,956,354 B2
(45) Date of Patent: Feb. 17, 2015

(54) ANTI-STICKING ELECTROSURGICAL INSTRUMENT

(75) Inventors: Yen-Ming Yeh, New Taipei (TW); Kuei-Huang Wu, Dasi/Taoyuan (TW); Chun-Da Ciou, Taichung (TW)

(73) Assignees: Advanced Medical Design Co., Ltd. (TW); Precision Machinery Research & Development Center (TW)

( * ) Notice: Subject to any disclaimer, the term of this patent is extended or adjusted under 35 U.S.C. 154(b) by 371 days.

(21) Appl. No.: 13/548,206

(22) Filed: Jul. 13, 2012

(65) Prior Publication Data

US 2014/0018801 A1    Jan. 16, 2014

(51) Int. Cl.
  *A61B 18/18* (2006.01)
  *A61B 18/14* (2006.01)

(52) U.S. Cl.
  CPC ................... *A61B 18/1402* (2013.01)
  USPC ........................................................... 606/45

(58) Field of Classification Search
  USPC ........................................................... 606/45
  See application file for complete search history.

(56) References Cited

U.S. PATENT DOCUMENTS

2009/0112200 A1*  4/2009  Eggers ............................ 606/29
2014/0171924 A1*  6/2014  Janssen et al. .................... 606/1

* cited by examiner

*Primary Examiner* — Rex R Holmes

(57) ABSTRACT

The present invention relates to a non-stick coated electrosurgical diathermy instrumentation, comprising: a handle portion; an isolation tube, connected to the handle portion by one end thereof; an instrument portion, connected to another end of the isolation tube, wherein an anti-sticking layer is formed on the surface of the instrument portion; and an electrode, connected to the handle portion and an external conductive member. In the present invention, the instrument portion is able to generate heat when the conductive member conducts electricity to the instrument portion.

5 Claims, 3 Drawing Sheets

ANTI-STICKING ELECTROSURGICAL INSTRUMENT

BACKGROUND OF THE INVENTION

1. Technical Field

The present invention relates to an electrosurgical instrument and more particularly to an anti-sticking electrosurgical instrument for preventing the instrument form sticking to the target organizations by coating an anti-sticking layer on the surface of the electrosurgical instrument.

2. Description of Related Art

Minimally invasive surgery is an important development in medical technology, wherein when operating the minimally invasive surgery to a patient, it merely causes minor trauma and small wound on the patient's body. So that, compared with the traditional surgery, the minimally invasive surgery includes the advantages of small incision, less trauma, rapid recovery and less pain for patients, and such advantages of the minimally invasive surgery also bring the revolution for modern medical technology.

For example, in the minimally invasive laparoscopic surgery, the surgeon would use several kinds of long-handled surgical instruments to finish the actions of cutting, moving, or clamping in the body cavity with a small space. Wherein the electrosurgical unit which is configured with the minimally invasive electrosurgical instrument (e.g., scissors, clamps) would emit high-frequency current on the sharp-edge, and then the surgeon would make cautery cut, cauterize, peel, or clamp the surgical targets.

However, such electrosurgical instrument includes the shortcomings and drawbacks as follows:
1. The electrosurgical instrument would stick to the target organizations in surgery, in this time, if the surgeon pull out electrosurgical instrument with a external force, it would cause expanding the wound, repeating bleeding, extending the surgery time, or affecting the success rate of the surgery. In addition, because of the misdistribution of the current on the electrode surface, the electrode surface would produce local high temperature, resulting in sticking, and poor conductivity, such that the electrosurgical instrument must to be cleaned.
2. In general, the electrosurgical instrument would be coated on teflon or silicon to achieve the effect of sticking, because the teflon or silicone could reduce the work of the instrument surface and the local high temperature. However, teflon or silicone would react to volatile the gas with fluorine and silicon due to the high temperature in the surgery, and then cause secondary pollution problems.

Accordingly, in view of the shortcoming of the conventional stylus, the inventor of the present application has made great efforts to make inventive research thereon and eventually provided an anti-sticking electrosurgical instrument.

BRIEF SUMMARY OF THE INVENTION

The first objective of the present invention is to provide an anti-sticking electrosurgical instrument for avoiding the electrosurgical instrument from sticking to the target organizations in surgery, the anti-sticking layer is coated on the surface of the instrument portion for preventing expanding the wound, repeating bleeding, extending the surgery time, or affecting the success rate of the surgery. In addition, the anti-sticking layer can also improve the conductivity and resistance to clean, wherein such features could prevent the sticking after long-term use.

The second objective of the present invention is to provide an anti-sticking electrosurgical instrument for changing the known material (such as teflon or silicone) to make the anti-sticking layer, for avoiding volatile toxic gas when the material is operated at high temperature, causing the secondary pollution.

Accordingly, for achieving the above objectives of the present invention, the inventors propose an anti-sticking electrosurgical instrument, comprising:
a handle portion;
an isolation tube, connected to the handle portion 1 by one end thereof;
an instrument portion, connected to another end of the isolation tube and driven by the handle portion via the isolation tube, wherein an anti-sticking layer is formed on the surface of the instrument portion; and
an electrode, connected to the handle portion and an external conductive member, such that the instrument portion is able to generate heat when the conductive member conducts electricity to the instrument portion.

BRIEF DESCRIPTION OF THE SEVERAL VIEWS OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE INVENTION

Figure 1:
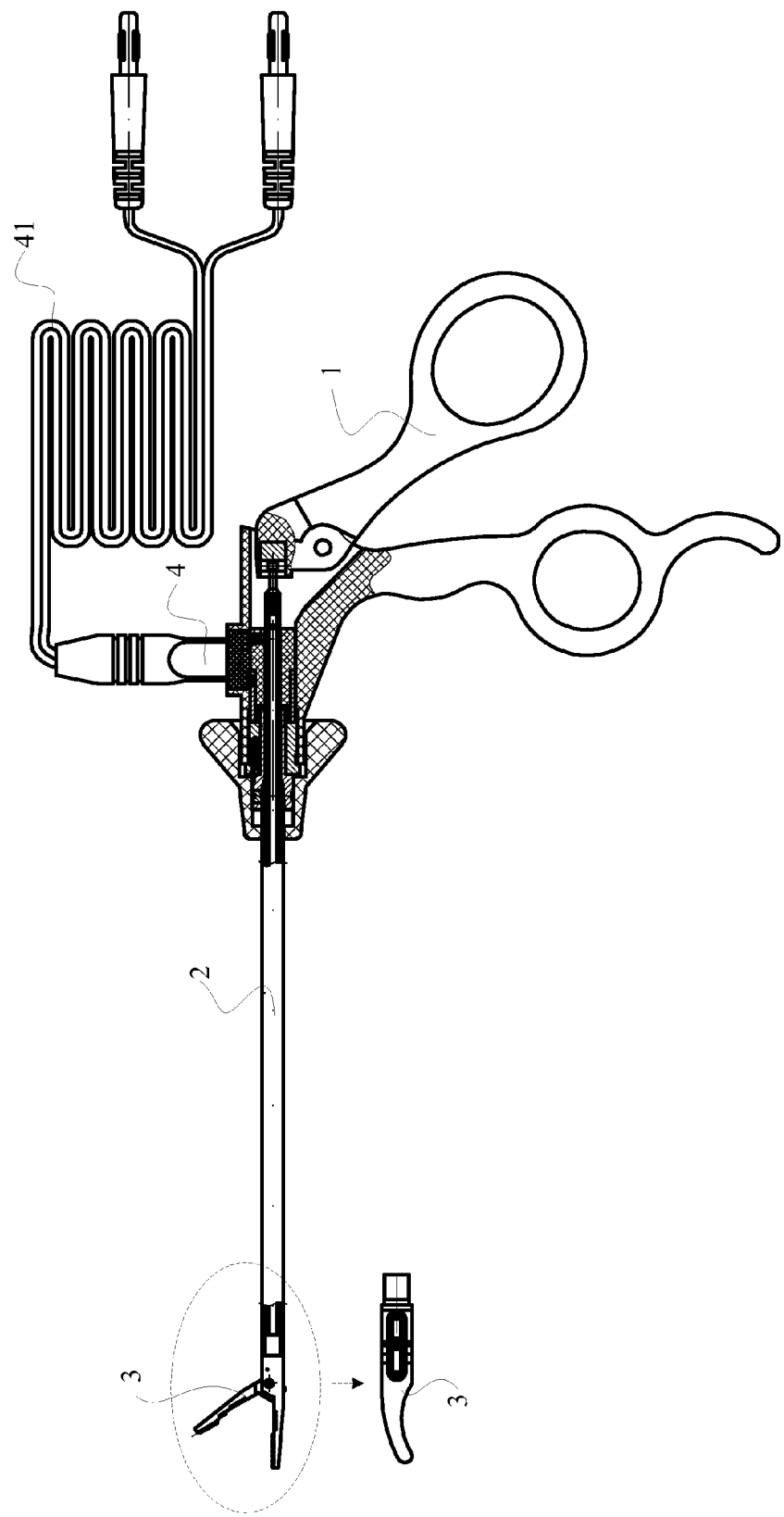
FIG. 1 is an appearance view of a first embodiment for an anti-sticking electrosurgical instrument according to the present invention.

To more clearly describe an anti-sticking electrosurgical instrument according to the present invention, embodiments of the present invention will be described in detail with reference to the attached drawings hereinafter:

With reference to FIG. 1, there is shown an appearance view of a first embodiment for the anti-sticking electrosurgical instrument according to the present invention. As shown in FIG. 1, the anti-sticking electrosurgical instrument includes: a handle portion 1, an isolation tube 2, an instrument portion 3, and an electrode 4, wherein the isolation tube 2 is connected to the handle portion 1 by one end thereof, and the instrument portion 3 is connected to another end of the isolation tube 2 and provided with an anti-sticking layer is formed on the surface thereof. In anti-sticking electrosurgical instrument, the instrument portion 3 can be driven by the handle portion 1 via the isolation tube 2; In addition, in the first embodiment of the instrument portion 3, the instrument portion 3 is a clamp. The electrode 4 is connected to the handle portion 1 and an external conductive member 41, such that the instrument portion 3 is able to generate heat when the conductive member 41 conducts electricity to the instrument portion 3.

Following description is the explanation for the anti-sticking layer. In this first embodiment, the anti-sticking layer is coated on the surface of the instrument portion 3 by magnetron sputtering physical vapor deposition (PVD), and the thickness of the anti-sticking layer is at least 0.5 μm. When processing the PVD, the temperature in PVD can be controlled for avoiding the heat deformation of the instrument. Besides, the anti-sticking layer can also be made of chromium metal oxide, zirconium metal oxide, chromium metal nitride, zirconium metal nitride, gold, silver or other material with chemical passivity. By this way, the anti-sticking layer would have functions of biologically compatibility, high temperature resistance, corrosion resistance, high hardness, high wear resistance, and easy to be cleaned, such that the instrument portion 3 can be avoided from resulting in the adverse of the surgery caused by reacting with the body organizations, releasing the harmful ions and sticking body organizations. In addition, the adhesion of the anti-sticking layer is at least HF3 (defined from the indentation test specification, the VDI 3198 standard 1991), and water contact angle of the non-sticking layer is at least 90°.

Figure 2:
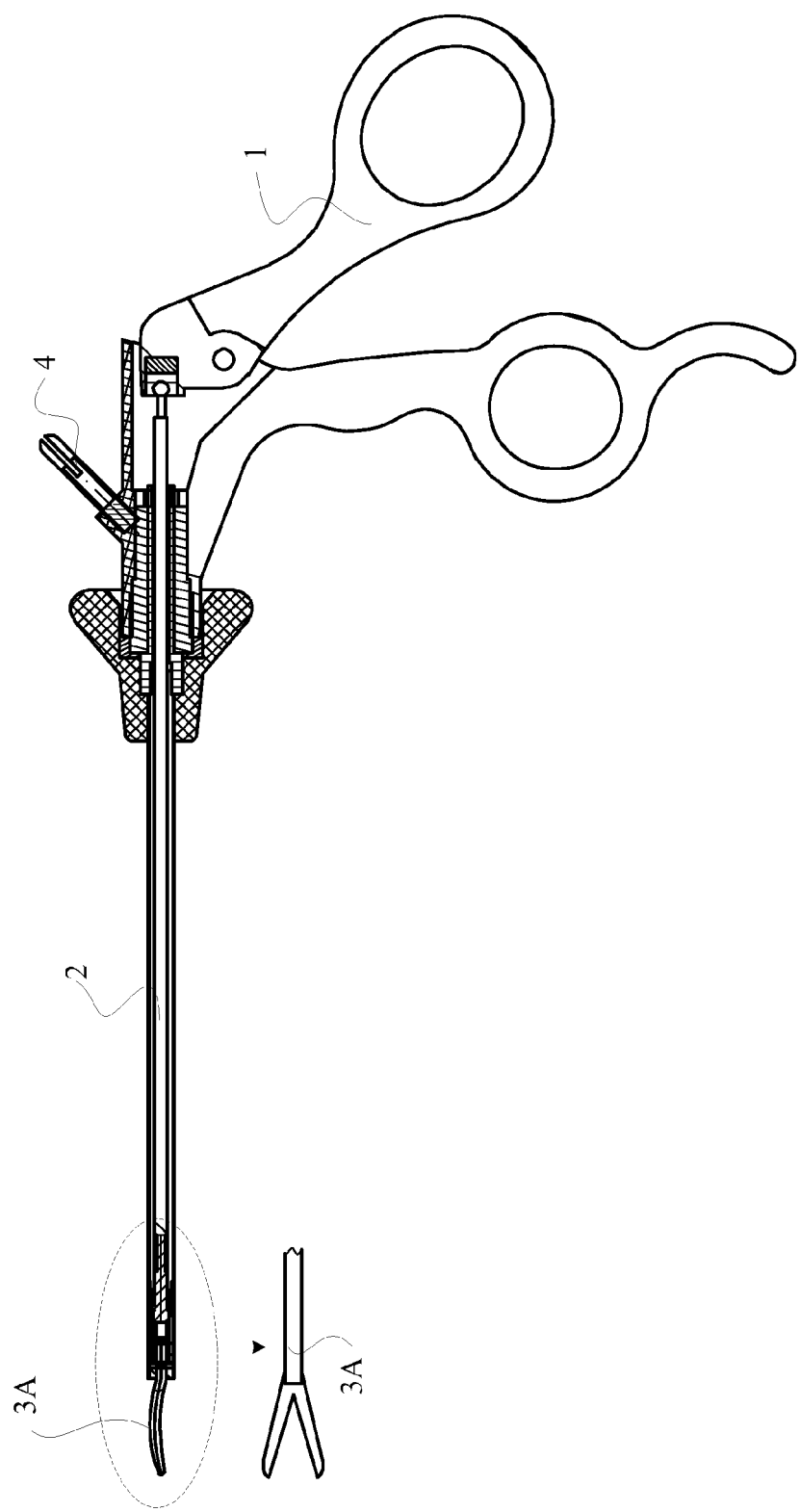
FIG. 2 is an appearance view of a second embodiment for the anti-sticking electrosurgical instrument according to the present invention.

With reference to FIG. 2, there is shown an appearance view of a second embodiment for the anti-sticking electrosurgical instrument according to the present invention. Comparing FIG. 2 with FIG. 1, it can easily find that the difference between the first embodiment and the second embodiment is that the instrument portion 3 is substituted for scissors 3A.

Figure 3:
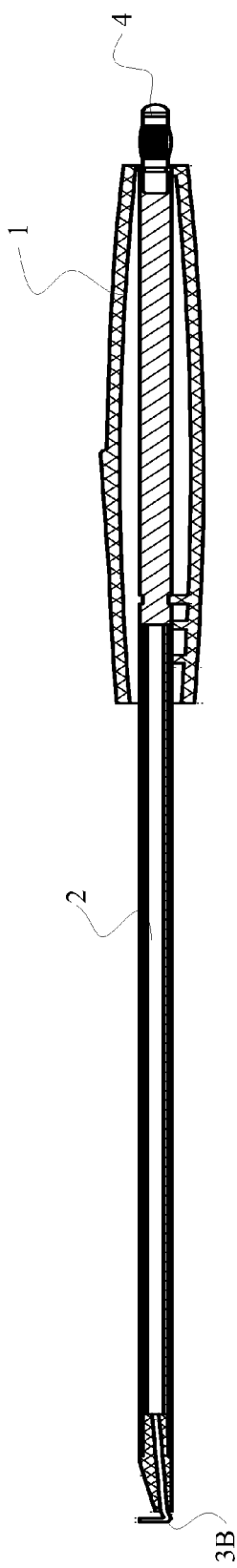
FIG. 3 is an appearance diagram of a third embodiment for the anti-sticking electrosurgical instrument according to the present invention.

Finally, with reference to FIG. 3, there is shown an appearance view of a third embodiment for the anti-sticking electrosurgical instrument according to the present invention. Comparing FIG. 3 with FIG. 1, the difference between the first embodiment and the third embodiment is that the instrument portion 3 is replaced by mono-polar electrosurgery 3B.

In addition to the above mentioned embodiments, the instrument portion 3 in the present invention could be substituted for any kinds of instrument which can be used in the surgery. Moreover, because the instrument portion is coated on the anti-sticking layer, the instrument portion would achieve the effect of anti-sticking.

In the end, the present invention has been completely and clearly disclosed in the above description, and in summary, the present invention has the following advantages:

To avoid the electrosurgical instrument from sticking to the target organizations in surgery, the anti-sticking layer is coated on the surface of the instrument portion for preventing from expanding the wound, repeating bleeding, extending the surgery time, or affecting the success rate of the surgery. In addition, the anti-sticking layer can also improve the conductivity and resistance to clean, wherein such features could prevent the sticking after long-term use.

The anti-sticking layer is made of chromium metal oxide, zirconium metal oxide, chromium metal nitride, or zirconium metal nitride, resulting in biologically compatible, high temperature resistance, corrosion resistance, high hardness, attrition resistance and resistance to clean of the anti-sticking layer. And such feature can avoid the instrument portion from reacting with the body organizations, and then prevent from releasing the harmful ions or sticking body organizations, resulting in the adverce of the surgery.

The above description is made on embodiments of the present invention. However, the embodiments are not intended to limit scope of the present invention, and all equivalent implementations or alterations within the spirit of the present invention still fall within the scope of the present invention.

We claim:

1. An anti-sticking electrosurgical instrument, comprising:
   a handle portion;
   an isolation tube, being connected to the handle portion by one end thereof;
   an instrument portion, being connected to another end of the isolation tube and driven by the handle portion via the isolation tube;
   an anti-sticking layer, being formed on surface of the instrument portion, wherein water contact angle of the anti-sticking layer is at least 90 degrees; and
   an electrode, being connected to the handle portion and an external conductive member, such that the instrument portion is able to generate heat when the conductive member conducts electricity to the instrument portion;
   wherein material of the anti-sticking layer is selected from the group consisting of: chromium metal oxide, zirconium metal oxide, chromium metal nitride, and zirconium metal nitride.

2. The anti-sticking electrosurgical instrument of claim 1, wherein thickness of the anti-stick layer is at least 0.5 μm.

3. The anti-sticking electrosurgical instrument of claim 1, wherein adhesion of the anti-sticking layer is at least HF3.

4. The anti-sticking electrosurgical instrument of claim 1, wherein the anti-sticking layer is coated on surface of the instrument portion by magnetron sputtering physical vapor deposition (PVD).

5. The anti-sticking electrosurgical instrument of claim 1, wherein the instrument portion is selected from the group consisting of: mono-polar electrosurgery, bipolar electrosurgery, scissors, clamps, and scalpel.

* * * * *